US010514385B2

(12) United States Patent
Ausdenmoore et al.

(10) Patent No.: US 10,514,385 B2
(45) Date of Patent: Dec. 24, 2019

(54) HEMATOLOGY ANALYZER, METHOD, AND SYSTEM FOR QUALITY CONTROL MEASUREMENTS

(75) Inventors: James Ausdenmoore, Gurnee, IL (US); Peter Osella, Chicago, IL (US); Ralph Taylor, Hawthorne Woods, IL (US)

(73) Assignee: SYSMEX CORPORATION, Hyogo (JP)

( * ) Notice: Subject to any disclaimer, the term of this patent is extended or adjusted under 35 U.S.C. 154(b) by 231 days.

(21) Appl. No.: 13/189,175

(22) Filed: Jul. 22, 2011

(65) Prior Publication Data

US 2013/0023006 A1    Jan. 24, 2013

(51) Int. Cl.
  *G01N 35/00*    (2006.01)
(52) U.S. Cl.
  CPC . *G01N 35/00663* (2013.01); *G01N 35/00603* (2013.01); *G01N 35/00623* (2013.01)
(58) Field of Classification Search
  USPC .................................................. 436/43–54
  See application file for complete search history.

(56) References Cited

U.S. PATENT DOCUMENTS

| 4,202,033 | A | * | 5/1980 | Strobel | ................. | G01N 33/49 |
| | | | | | | 436/183 |
| 4,731,726 | A | | 3/1988 | Allen | | |
| 4,757,437 | A | | 7/1988 | Nishimura | | |
| 5,211,310 | A | | 5/1993 | Godolphin et al. | | |
| 5,367,888 | A | | 11/1994 | Muston et al. | | |
| 5,413,246 | A | | 5/1995 | Godolphin et al. | | |
| 5,441,415 | A | | 8/1995 | Lee et al. | | |

(Continued)

FOREIGN PATENT DOCUMENTS

| JP | H09-043245 A | 2/1997 |
| JP | 2008-032493 A | 2/2008 |

(Continued)

OTHER PUBLICATIONS

Coulter HmX Hematology Analyzer with Autoloader, *Operator Guide*, http://www.frankshospitalworkshop.com/equipment/documents/automated_analyzer/user_manuals/Coulter_HmX_Analyzer_User_Guide.pdf, Jun. 1999, 128 pages.

(Continued)

*Primary Examiner* — Christopher Adam Hixson
*Assistant Examiner* — Michelle Adams
(74) *Attorney, Agent, or Firm* — Brinks Gilson & Lione

(57) ABSTRACT

An analyzer for measuring a sample includes a display, measurement hardware configured to perform a quality control measurement on a vial containing a quality control (QC) sample, and a controller. The controller is in communication with the display and the measurement hardware and is configured to communicate, via the display, instructions to implement a QC measurement on a first vial containing a first QC sample. If a result of the QC measurement is within a pre-determined range the first vial passes the QC measurement. If the result of the QC measurement is not within the pre-determined range the first vial fails the QC measurement. If the first vial fails the QC measurement and if a number of times the first vial fails the QC measurement is less than a predetermined number, the controller is configured to communicate, via the display, instructions to repeat the QC measurement on the first vial.

14 Claims, 14 Drawing Sheets

(56) References Cited

U.S. PATENT DOCUMENTS

| | | | |
|---|---|---|---|
| 5,577,837 | A | 11/1996 | Martin et al. |
| 5,590,057 | A | 12/1996 | Fletcher et al. |
| 5,743,250 | A | 4/1998 | Gonda et al. |
| 5,788,508 | A | 8/1998 | Lee et al. |
| 5,791,907 | A | 8/1998 | Ramshaw et al. |
| 5,882,206 | A | 3/1999 | Gillio |
| 6,319,718 | B1 | 11/2001 | Matsubara et al. |
| 6,371,765 | B1 | 4/2002 | Wall et al. |
| 6,386,882 | B1 | 5/2002 | Linberg |
| 6,535,714 | B2 | 3/2003 | Melker et al. |
| 6,549,876 | B1 * | 4/2003 | Yundt-Pacheco ...... G01D 21/00 702/182 |
| 6,772,650 | B2 | 8/2004 | Ohyama et al. |
| 6,834,207 | B2 | 12/2004 | Miyauchi et al. |
| 6,938,502 | B2 | 9/2005 | Tanoshima et al. |
| 6,991,464 | B2 | 1/2006 | Liebert |
| 7,013,260 | B2 | 3/2006 | Asada |
| 7,357,640 | B2 | 4/2008 | Berman |
| 7,505,557 | B2 | 3/2009 | Modica et al. |
| 7,777,763 | B2 | 8/2010 | Haakonsen et al. |
| 8,158,439 | B2 | 4/2012 | Shibata |
| 8,562,357 | B2 | 10/2013 | Pfingsten et al. |
| 8,793,212 | B2 | 7/2014 | McGuire |
| 2002/0103642 | A1 | 8/2002 | Asada |
| 2002/0106622 | A1 | 8/2002 | Osborne et al. |
| 2003/0070498 | A1 | 4/2003 | Ohyama et al. |
| 2003/0120462 | A1 | 6/2003 | Yundt-Pacheco |
| 2003/0154067 | A1 | 8/2003 | Wen et al. |
| 2004/0059599 | A1 | 3/2004 | McIvor |
| 2004/0260165 | A1 | 12/2004 | Cho et al. |
| 2005/0037502 | A1 * | 2/2005 | Miller .......................... 436/43 |
| 2005/0070777 | A1 | 3/2005 | Cho et al. |
| 2005/0074361 | A1 | 4/2005 | Tanoshima et al. |
| 2005/0159982 | A1 * | 7/2005 | Showalter ............. G06F 19/366 705/2 |
| 2005/0165554 | A1 | 7/2005 | Betancourt et al. |
| 2005/0255600 | A1 | 11/2005 | Padmanabhan et al. |
| 2006/0009949 | A1 | 1/2006 | Seher et al. |
| 2006/0029520 | A1 | 2/2006 | Tanoshima et al. |
| 2006/0040245 | A1 | 2/2006 | Airola et al. |
| 2006/0072028 | A1 | 4/2006 | Hong |
| 2006/0166366 | A1 | 7/2006 | Matsumoto et al. |
| 2006/0167371 | A1 | 7/2006 | Flaherty et al. |
| 2007/0054404 | A1 | 3/2007 | Huo et al. |
| 2007/0158247 | A1 | 7/2007 | Carr et al. |
| 2008/0020361 | A1 | 1/2008 | Kron et al. |
| 2008/0038706 | A1 | 2/2008 | Dameshek |
| 2008/0057484 | A1 | 3/2008 | Miyata et al. |
| 2008/0076109 | A1 | 3/2008 | Berman |
| 2008/0113438 | A1 | 5/2008 | Ortiz et al. |
| 2008/0160492 | A1 | 7/2008 | Campbell et al. |
| 2008/0171311 | A1 | 7/2008 | Centen et al. |
| 2008/0186133 | A1 | 8/2008 | Parkhurst et al. |
| 2008/0186134 | A1 | 8/2008 | Parkhurst et al. |
| 2008/0219887 | A1 * | 9/2008 | Akutsu .......................... 422/67 |
| 2008/0254426 | A1 | 10/2008 | Cohen |
| 2008/0268494 | A1 | 10/2008 | Linssen |
| 2008/0312893 | A1 | 12/2008 | Denton |
| 2009/0017887 | A1 | 1/2009 | Montocchio |
| 2009/0116536 | A1 | 5/2009 | Amato |
| 2009/0123903 | A1 | 5/2009 | Weitenberner |
| 2009/0148821 | A1 | 6/2009 | Carkner et al. |
| 2009/0231134 | A1 | 9/2009 | Modica et al. |
| 2010/0092936 | A1 | 4/2010 | Pfingsten et al. |
| 2010/0191583 | A1 | 7/2010 | Mackenzie |
| 2010/0240079 | A1 | 9/2010 | Jackson |
| 2010/0256990 | A1 | 10/2010 | Horiguchi et al. |
| 2010/0266998 | A1 | 10/2010 | Tashiro et al. |
| 2011/0306023 | A1 | 12/2011 | Blank et al. |
| 2012/0036944 | A1 | 2/2012 | Chida et al. |
| 2012/0046606 | A1 | 2/2012 | Arefieg |
| 2012/0064497 | A1 | 3/2012 | Wu |
| 2012/0209783 | A1 | 8/2012 | Smith et al. |
| 2013/0132298 | A1 | 5/2013 | Subhanjan |

FOREIGN PATENT DOCUMENTS

| | | |
|---|---|---|
| JP | 2009-036515 A | 2/2009 |
| WO | WO 01/14912 A1 * | 3/2001 |
| WO | WO-2007/023205 A1 * | 3/2007 |

OTHER PUBLICATIONS

Coulter LH 500 Hematology Analyzer, Training Modules, PN624762CA, Miami Education Center, https://www.beckmancoulter.com/ucm/idc/groups/public/documents/webasset/glb_bci_150462.pdf, Sep. 2009, 234 pages.

Daqing, Luosang, "Quality Assurance before Hematology Analysis", *Tibet's Science and Technology*, No. 9, Issue No. 161, 2006, 9 pages.

Deprez et al., "Evaluation of the pocH-100iV DIFF Hematology Analyzer for Use in Horses and Cattle", *Vlaams Diergeneeskundig Tijdchrift*, 78, 2009, pp. 105-109.

Diagnostics, "FDA Grants Clearance for Automated CBC Analyzer", *Medical Devices and Surgical Technology Week*, Atlanta, Mar. 28, 2004, 3 pages.

JS Countdown Timer ON Submit Button, *Webdeveloper Webpages*, http://www.webdeveloper.com/forum/showthread/php?154969-JS-countdown-timer-ON-submit-button, Jul. 2007, 1 page.

LH 750 Hematology Analyzer, LH Slidemaker, LH Slidestainer, PN 4277276EA, Miami Education Center, http://bluecoat-02/?cfru=aHR0cDovL3ZkdC51Z2VudC5iZS9jb2RIL3Nob3d1cGxvYWQuc GhwP2IkPTQ3OA==, Jul. 2009, 314 pages.

LH 780 Hematology Analyzer, With Optional LH Slidemaker and LH Slidestainer, PN A35575BA, Miami Education Center, Jul. 2009, 294 pages.

Meditrade, Sysmex PocH 100i, http://www.meditrade.si/slo/index.php?cid=270, Aug. 22, 2004, 4 pages.

Narayanan, S., "Preanalytical Issues Related to Blood Sampling Mixing", *AEFA Webpages*, http://www.aefa.es/wp-content/uploads/2014/04/Preanalytical-issues-related-blood-sample-mixing.pdf, Oct. 2005, 8 pages.

Omnipod Insulin Management System, *Insulet Corporation Caregiver Guide*, https://www.myomnipod.com/pdf/CaregiverGuide.pdf, May 2008, 11 pages.

Pegiterferon Alfa-2a, *NIG GOV Webpages*, Way Back Machine, https://web.archive.org/web/20100411115439/http://www.nlmnih.gov/medlineplus/druginfo/meds/a605029.html, Apr. 2010, 4 pages.

Poch 100i, Vital Information on the Spot, http://www.cruinn.ie/_fileUpload/Image/Drawings/Pchi-100i[7676].pdf, 2003, 4 pages.

POCH-100i enters the second round, Sysmex 2008, 3 pages.

Sysmex Automated Hematology Analyzer pocH-100i Instructions for Use, North American Edition, Sysmex Corporation, Kobe, Japan, Jun. 2008, 119 pages.

Sysmex pocH 100, Sysmex webpages, pocH 100 features, archives org, Nov. 19, 2008.

Urakawa, K, "Ultimate Stopwatch and Timer", *Youtube Webpages*, https://www.youtube.com/watch?v=9iEqx4d0cHA, uploaded Feb. 2010, 1 page.

Office Action for U.S. Appl. No. 13/189,158 dated Jun. 24, 2015, 23 pages.

Office Action for U.S. Appl. No. 13/189,158 dated May 1, 2012, 26 pages.

Office Action for U.S. Appl. No. 13/189,158 dated Nov. 7, 2012, 21 pages.

Office Action for U.S. Appl. No. 13/189,158 dated Oct. 9, 2014, 43 pages.

Notice of Allowance for U.S. Appl. No. 13/189,193 dated Aug. 27, 2015, 17 pages.

Office Action for U.S. Appl. No. 13/189,193 dated Jun. 23, 2015, 18 pages.

Office Action for U.S. Appl. No. 13/189,193 dated May 21, 2012, 26 pages.

Office Action for U.S. Appl. No. 13/189,193 dated Nov. 15, 2012, 23 pages.

(56) References Cited

OTHER PUBLICATIONS

Office Action for U.S. Appl. No. 13/189,193 dated Oct. 10, 2014, 47 pages.

* cited by examiner

HEMATOLOGY ANALYZER, METHOD, AND SYSTEM FOR QUALITY CONTROL MEASUREMENTS

BACKGROUND i) Field

This application relates to an analyzer and its components. In particular, this application relates to a clinical analyzer and system configured to ensure that an operator is qualified to use the analyzer and that the operator adheres to certain procedures while operating the analyzer.

ii) Description of the Related Art

Hematology analyzers are utilized to make various measurements of the constituents of a blood sample. Many known hematology analyzers are large cumbersome machines placed in hospitals and laboratories. Such analyzers are required to be operated by an operator officially certified to operate the analyzers.

Smaller hematology analyzers, such as the analyzers described in U.S. Pat. Nos. 6,772,650 and 7,013,260, are designed to be placed in a doctor's office where space is at a premium. Like the analyzers described above, a certified operator may operate these machines.

However, it is difficult to guarantee that such an operator is actually operating the analyzer. In many instances, the person operating the machine may have little or no training on the analyzer. Even when trained, the operator may not follow the various procedures required for accurate testing of a patient blood sample.

For example, performance of a quality control check of the analyzer may be required on a periodic basis to ensure that the analyzer is operating correctly. To perform the quality control check, various samples with known consistencies are inserted into the analyzer for analysis. However, in many instances the samples must be thoroughly mixed before measurement. When the operator skips this step, the samples may become unusable for future quality control checks as the consistency of the samples may change. Thus, a new sample may be required, which will necessarily increase the cost associated with operation of the analyzer.

In other instances, an operator may attempt to measure a patient blood sample that has been in storage. In this case, it may be necessary to treat the patient blood sample prior to measurement to ensure accuracy of measurement. For example, the patient blood sample may need to be mixed. When an operator fails to perform this procedure correctly, the measurement may fail or give inaccurate results.

Other problems with known analyzers will become apparent upon reading the descriptions of the various embodiments described below.

SUMMARY

In one aspect, an analyzer for measuring a sample includes a display, measurement hardware configured to perform a quality control measurement on a vial containing a quality control (QC) sample, and a controller. The controller is in communication with the display and the measurement hardware and is configured to communicate, via the display, instructions to implement a QC measurement on a first vial containing a first QC sample. If a result of the QC measurement is within a pre-determined range the first vial passes the QC measurement. If the result of the QC measurement is not within the pre-determined range the first vial fails the QC measurement. If the first vial fails the QC measurement and if a number of times the first vial fails the QC measurement is less than a predetermined number, the controller is configured to communicate, via the display, instructions to repeat the QC measurement on the first vial.

In a second aspect, a method for measuring a sample includes providing a display and measurement hardware configured to perform a quality control measurement on a vial containing a QC sample. The method also includes communicating, via the display, instructions to implement a QC measurement on a first vial containing a first QC sample. If a result of the QC measurement is within a pre-determined range, the first vial passes the QC measurement. If the result of the QC measurement is not within the pre-determined range, the first vial fails the QC measurement. If the first vial fails the QC measurement and if a number of times the first vial fails the QC measurement is less than a predetermined number, the method also includes communicating, via the display, instructions to repeat the QC measurement on the first vial.

In a third aspect, a non-transitory machine-readable storage includes at least one codes section that causes a machine to communicate instructions to implement a QC measurement on a first vial containing a first QC sample. If a result of the QC measurement is within a pre-determined range, the first vial passes the QC measurement. If the result of the QC measurement is not within the pre-determined range, the first vial fails the QC measurement. If the first vial fails the QC measurement and if a number of times the first vial fails the QC measurement is less than a predetermined number, the code section causes the machine to communicate instructions to repeat the QC measurement on the first vial.

BRIEF DESCRIPTION OF THE DRAWINGS

FIGS. 7A-13A are exemplary images that may be presented on a display of the hematology analyzer during the operations of FIG. 6;

DETAILED DESCRIPTION

The embodiments below describe an exemplary embodiment of an analyzer system. For example, the analyzer system may include a hematology analyzer configured to analyze a patient blood sample and a server in communication with the hematology analyzer. In particular, the system is configured to ensure that an operator is qualified to use the analyzer and that the operator adheres to certain procedures while operating the analyzer. In one embodiment, the analyzer system prevents an operator from using an analyzer until it can be confirmed that the operator is qualified to use the analyzer. In second and third embodiments, the operator is presented with step-by-step instructions that guide the operator in the proper use of the analyzer.

Figure 1:
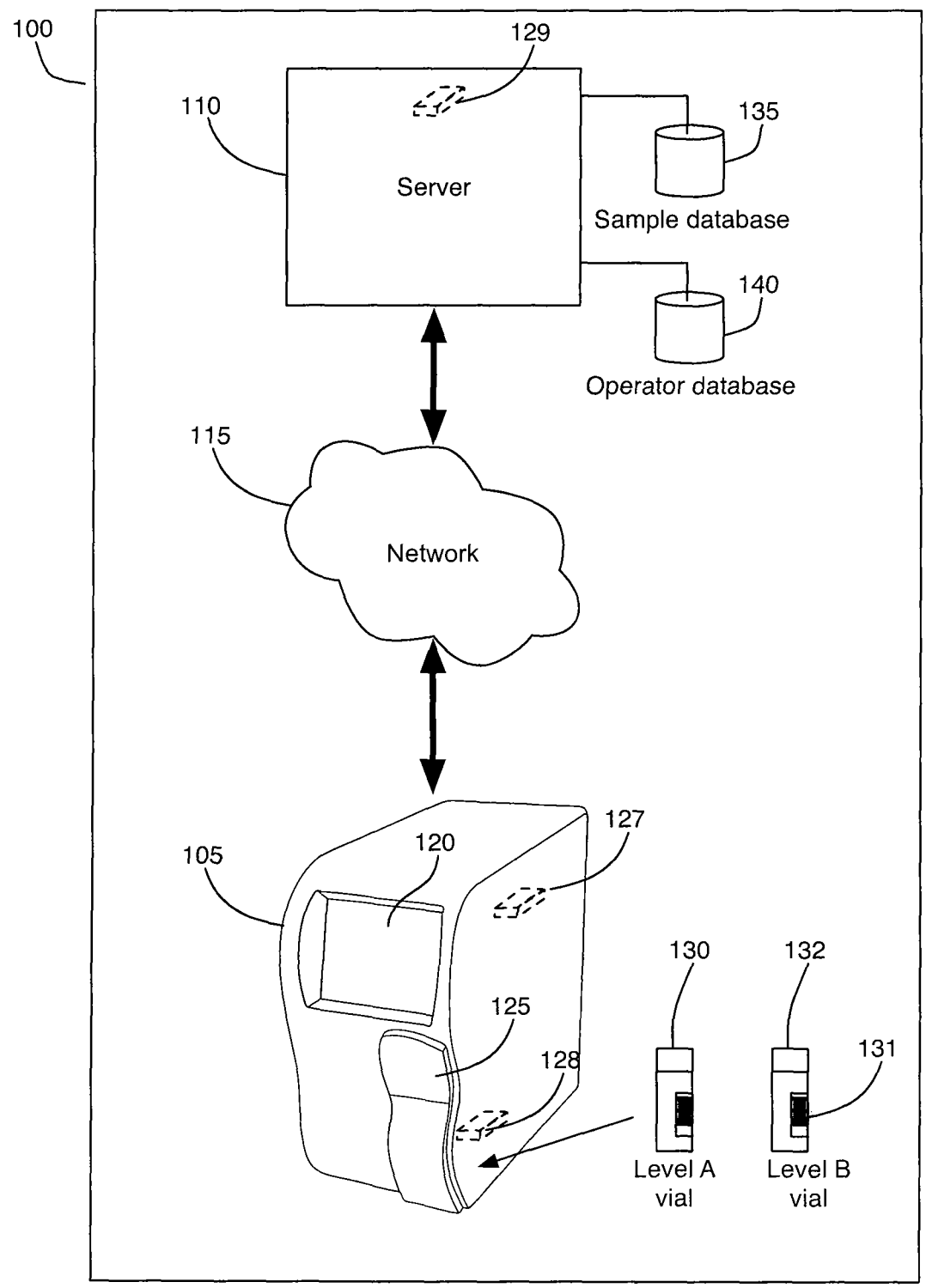
FIG. 1 is an exemplary system diagram of a hematology analyzer and server.

FIG. 1 is an exemplary hematology analyzer system 100 (hereinafter system). The system 100 includes a hematology analyzer 105 (hereinafter analyzer) and a server 110. The analyzer 105 may include the features of the analyzer of U.S. Pat. No. 6,772,650, which is hereby incorporated by references. For example, the analyzer 105 may include an input/display section 120, measurement hardware 125, and a controller 127.

The measurement hardware 128 may include a sample-setting panel 125 provided on a lower front right portion of the analyzer 105. The sample-setting panel 125 is configured to be opened and closed to facilitate placement of one or more sample vials 130 and 132 in a sample setting section (See FIG. 12B) that is configured to measure the consistency of samples.

The controller 127 may correspond to an Intel®, AMD®, or PowerPC® based microprocessor system or a different microprocessor system. The controller 127 may include an operating system, such as a Microsoft Windows®, Linux, Unix® based operating system or a different operating system. The controller 127 may be configured to communicate with other computers, such as the server 110, via a network 115. The controller 127 may be configured to control the operation of the analyzer 105. In this regard, the controller 127 may be configured to generate images and to communicate the images to the input/display section 120. The controller 127 may also be configured to cooperate with the measurement hardware 125 to perform various measurements. For example, the controller 127 may be operable to cause the measurement hardware 125 to dispense a samples from sample vials 130 and 132 and dilute the samples with various reagents to thereby and analyze constituents of the samples.

In one embodiment, two sample vials 130 and 132 are utilized to ensure that the analyzer 105 is calibrated. During normal operation, the analyzer 105 is utilized to determine whether constituents of a patient blood sample fall within various ranges that have upper and lower limits. The sample vials 130 and 132 comprise substances in known quantities configured such than when analyzed by the analyzer 105, a given metric should produce a result at one end or the other of a range associated with the metric. For example, consistency of substances in the first sample vial 130 may be configured to provide results at respective lower ends of the ranges. The consistency of Substances in the second sample vial 132 may be configured to provide results at respective upper ends of the ranges.

The sample vials 130 and 132 are generally provided in lots, where a first lot of sample vials contains sample vials with consistencies configured to provide results at a first level (e.g., lower end of the range of measured parameters), and a second lot of sample vials contains sample vials with consistencies configured to provide results at a second level (e.g., upper end of the range of measured parameters). Each sample vial 130 and 132 is prepared with known concentrations of substances and is provided with a barcode 131 that facilitates identification of a given sample. The barcode 131 and concentration information for each sample vial 130 and 132 is stored in a sample database 135.

The sample vials 130 and 132 may be used repeatedly. For example, the sample vials 130 and 132 may be utilized on daily basis when performing a quality control check of the analyzer 105, as described below. With each use, some material in the sample vial 130 and 132 is depleted. Thus, there is a finite number of times in which a given sample vial 130 and 132 may be utilized. In addition, the sample vials 130 and 132 may have an expiration date. Accordingly, the number of times for which a given sample vial 130 and 132 is used and the expiration date for each sample vial 130 and 132 may be stored in the sample database 135, so as to keep track of the usable life of the sample vial 130 and 132. In some implementations, the analyzer 105 is configured to prevent use of a given sample vial 130 and 132 when it has been used more than a predetermined number of times or passed its expiration date.

The input/display section 120 of the analyzer 105 is configured to provide instructions to an operator of the analyzer 105 and to receive input from the operator. The input/display section 120 may be positioned on a front upper portion of the analyzer 105 and may correspond to a touch sensitive display that enables operator input. In other implementations, operator input may come by way of a keyboard (now shown) coupled to the analyzer 105. As described below, via the input/display section 120, the operator may be questioned as to whether he is registered with the analyzer 105 and whether he has completed a training session (i.e., familiarization session). The operator may be instructed to insert various sample vials 130 and 132 into the analyzer 105 to determine whether the analyzer 105 is calibrated. The operator may be instructed on how the sample vials 130 and 132 and/or patient blood samples are to be handled prior to insertion into the sample-setting panel 125.

The server 110 may correspond to a computer system configured to communicate information to many analyzers 105, and to authorize the analyzers 105 for use. The server 110 may include a controller 129 and input/output logic that facilitates communication of data to and from a sample database 135 and an operator database 140.

The controller 129 may correspond to an Intel®, AMD®, or PowerPC® based microprocessor system or a different microprocessor system. The controller 129 may include an operating system, such as a Microsoft Windows®, Linux, Unix® based operating system or a different operating system. The controller 129 may be configured to communicate with other computers, such as the analyzer 105, via a network 115. The controller 129 may be configured to control the operation of the server 110. For example, the controller 129 may facilitate communication between the server 110 and the analyzer 105 via a network 115. The controller 129 may be operable to cause the server 110 to authorize the analyzer 105 on a periodic basis. For example, the analyzer 105 may be configured to prevent usage every twenty-four hours. In this case, the server 110 is configured to reauthorize the analyzer for usage on a daily basis subject to various requirements, which are described below.

The server 110 may be in communication with the sample database 135, which stores sample information. During operations, the server 110 may be configured to communicate the sample information to the analyzer 105 when requested by the analyzer 105. The analyzer 105 may store the information associated with a given sample internally.

The server 110 may also be in communication with the operator database 140. The operator database 140 stores information associated with operators authorized to operate a given analyzer 105. The operator information may include identifying information for each operator, such as the operator's name or an ID assigned to the operator. The operator information may also indicate a date on which the operator was authorized and information that identifies the analyzer 105 or analyzers for which the operator is authorized. The operator information may also specify whether the operator is currently authorized to use a given analyzer 105.

Figure 2:
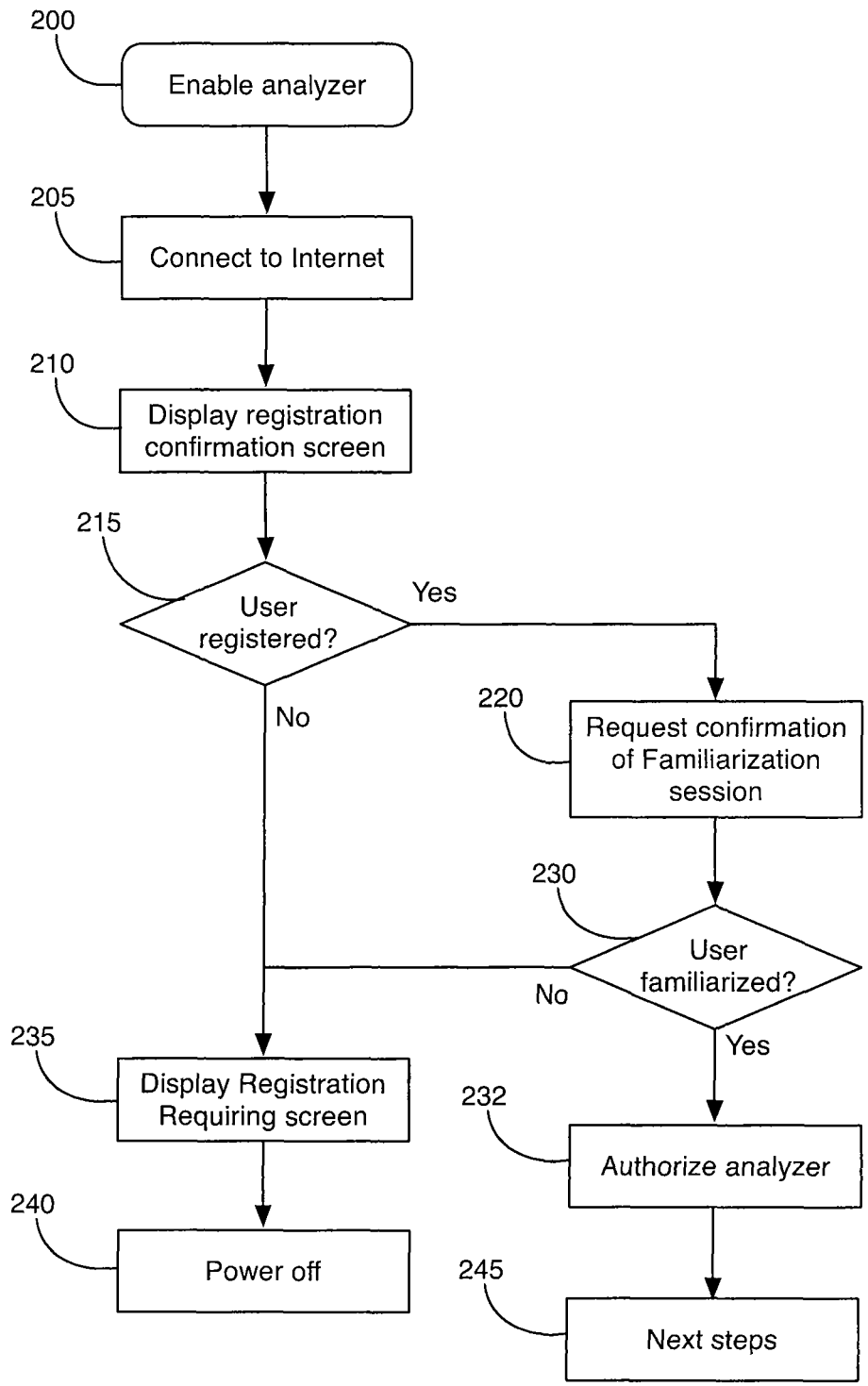
FIG. 2 is an exemplary block diagram of operations for confirming operator registration and training for the system of FIG. 1.
Figure 3A:
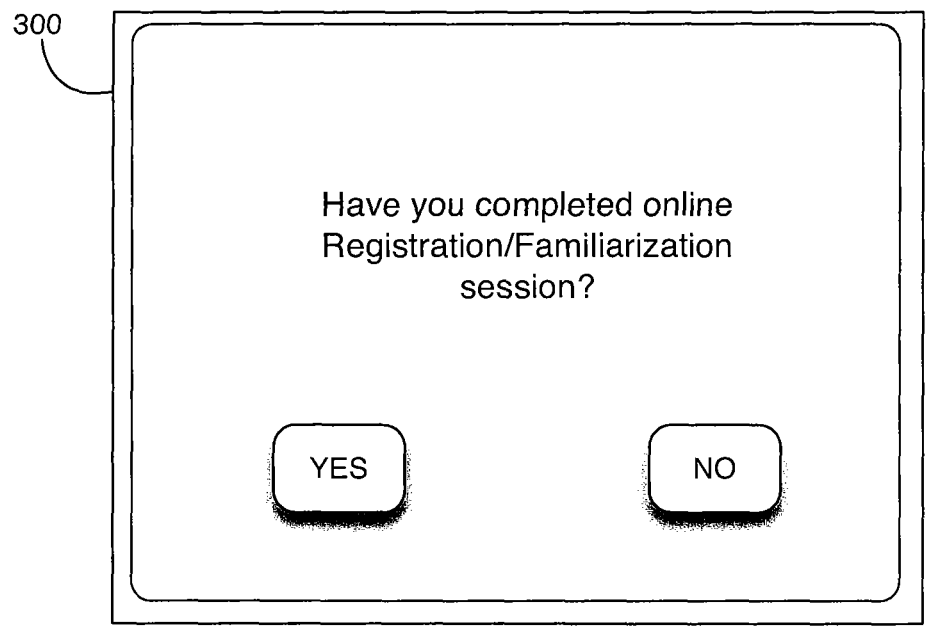
FIGS. 3A and 3B are exemplary images that may be presented on a display of the hematology analyzer during the operations of FIG. 2.

FIG. 2 illustrates exemplary operations that may be performed by an analyzer, such as the analyzer 105 described above or a different analyzer, to determine whether an operator is authorized to use the analyzer 105. The operations in FIG. 2 are best understood with reference to FIGS. 3A and 3B. Computer instructions for executing the operations may be stored in one or more non-transitory computer readable media of the analyzer 105, such as a computer memory that is in communication with the controller 127. The instructions may be executed by the controller 127 or any of the systems or processors described herein.

At block 200, the analyzer 105 is enabled by a predetermined event. For example, the analyzer 105 is enabled by being provided with power, the power switch of the analyzer 105 may be brought out of a standby state, and/or an operator may login to the analyzer 105.

At block 205, the analyzer 105 is connected to a network 115, such as the Internet. In this regard, an initial screen may be displayed on the input/display section 120 if the analyzer 105 is not connected to an Internet connection. The screen may inform an operator of the analyzer 105 to connect the analyzer 105 to a network connection before allowing the operator to proceed.

At block 210, a registration confirmation message may be displayed to the operator. For example, the registration/familiarization image 300 of FIG. 3A may be shown to the operator via the input/display section 120. The registration/familiarization image 300 requests the operator to confirm whether the operator has completed registration and has completed a familiarization session. In some implementations, the analyzer 105 may also ask the operator for identifying information. For example, before using the analyzer 105, operators may be required to first provide registration information, such as the operator's name, place of work, etc. The operator may be required to provide information that identifies the analyzer 105 the operator will utilize for testing samples, such as a serial number. The operator may provide other information. Operators may also be required to take some from of training on the operation of the analyzer 105, such as a class on the basic operations of the analyzer 105 that teaches procedures for using the analyzer 105 (e.g., how to insert samples and the like).

At block 215, if the operator indicates that he is registered, then at block 220, the analyzer 105 may communicate with the server 110 to confirm whether the operator has taken a familiarization session. For example, the analyzer 105 may send the operator identifying information to the server 110 via the network 115. The server 110 may then search the operator database 140 to locate the operator and confirm that the operator is registered and that the operator has completed the familiarization session.

At block 230, if the server 110 has confirmed operator familiarization, the server 110 may communicate this fact to the analyzer 105 at block 232. The analyzer 105 may then proceed with other operations at block 245.

If at block 230, the server 110 determines that the operator has not been familiarized and/or that the operator is not registered to operate the analyzer 105, then at block 235, the server 110 may communicate this fact to the analyzer 105.

Figure 3B:

In response, the analyzer 105 may display an image on the input/display section 120 informing the operator that registration and/or familiarization is required, such as the image 305 of FIG. 3B.

At block 240, the analyzer 105 may be powered off. Alternatively, the operations may repeat back to block 210.

Thus, the operations above prevent an unauthorized and/or un-familiarized operator from operating the analyzer 105. This helps to ensure that when samples are analyzed, they are analyzed with correct procedures.

Figure 4:
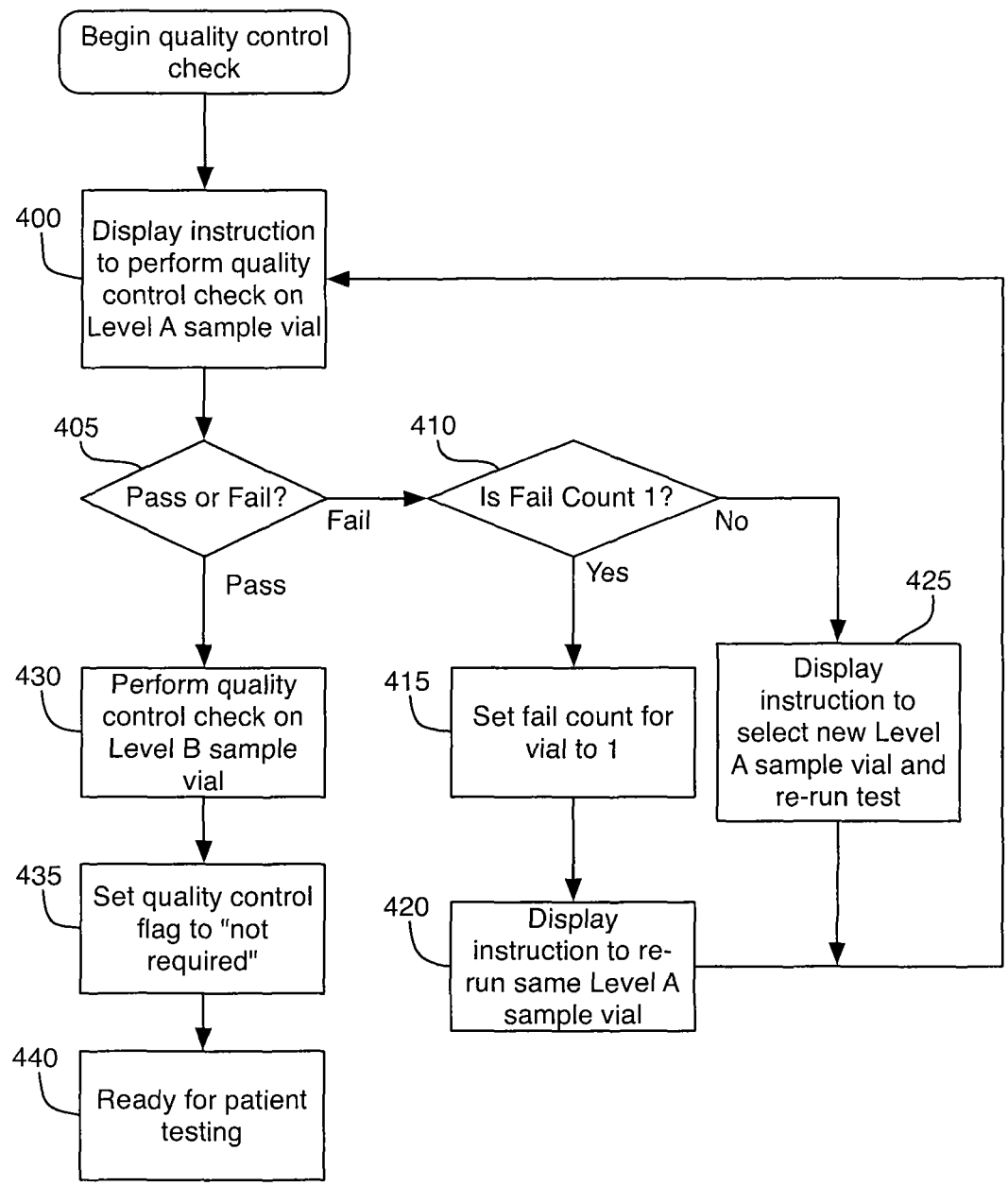
FIG. 4 is an exemplary block diagram for performing a quality control check of the hematology analyzer of FIG. 1.

FIG. 4 illustrates exemplary operations that may be performed by the analyzer 105 when performing a quality control check of the analyzer 105. Quality control checks are required to ensure that the analyzer is calibrated. In some implementations, the analyzer 105 may be configured to require a quality control check is performed on a periodic basis, such as 7:00 AM each morning, before allowing normal measurement procedures to occur. The operations in FIG. 4 are best understood with reference to FIGS. 5A and 5B. Computer instructions for executing the operations may be stored in one or more non-transitory computer readable media of the analyzer 105, such as a computer memory that is in communication with the controller 127. The instructions may be executed by the controller 127 or any of the systems or processors described herein.

At block 400, instructions for performing a control check based on a level A sample vial 130 may be presented to the operator via the input/display section 120. The operator may then select a level A sample vial 130 and scan a barcode 131 of the level A sample vial 130. The operator then inserts the level A sample vial 130 into the sample-setting panel 125. The analyzer 105 may then measure the amount of various substances in the level A sample vial 130. The measurements are compared with known quantities of the substances associated with the specific level A sample vial 130. As noted above, data that defines the actual quantities of the substances for each vial is stored in the sample database 135 and can be located via the barcode 131. If a given level A sample vial 130 has been tested before, the actual quantities may be stored locally in the analyzer 105. Otherwise, the analyzer 105 communicates the barcode 131 to the server 110. The server 110 then responds with the actual quantities associated with the level A sample vial 130.

At block 405, the analyzer 105 determines whether the measurements are within an acceptable range of the known quantities of substances associated with the level A sample vial 130. If the measured quantities are out of range, then at block 410, the analyzer 105 determines whether this specific level A sample vial 130 has failed before.

If the level A sample vial 130 has not failed before, then at block 415, a failure count associated with the level A sample vial 130 is incremented. The failure count may be maintained within a memory of the analyzer 105. In addition or alternatively, the failure count may be communicated to the server 110 and stored in a record of the sample database 135 that is associated with the level A sample vial 130.

Figure 5A:
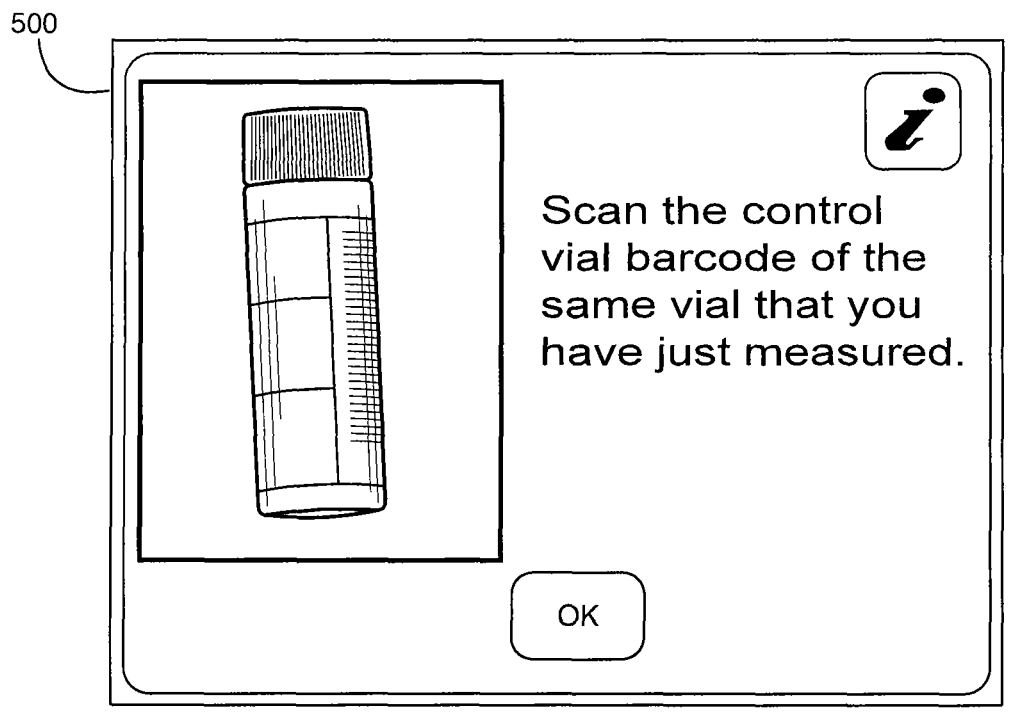
FIGS. 5A and 5B are exemplary images that may be presented on a display of the hematology analyzer during the operations of FIG. 4.
Figure 5B:
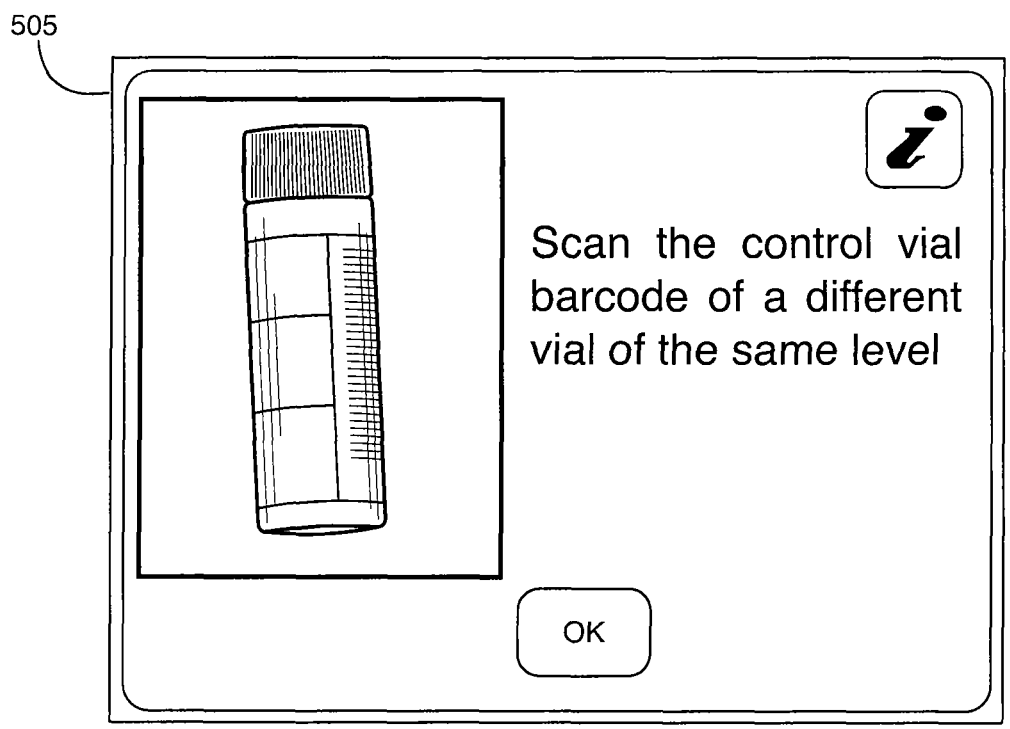

At block 420, the operator is instructed to retest the failed level A sample vial 130. FIG. 5A illustrates an exemplary image 500 that may be shown to the operator via the input/display section 120 to instruct the operator to retest the failed level A sample vial 130.

After the operator is instructed to retest the failed level A sample vial 130, the operations may repeat from block 400.

If at block 410, the failure count associated with the level A sample vial 130 is equal to one, the failure count may be incremented again. In some implementations, a second failure renders the level A sample vial 130 unusable for future quality control checks. As such, the level A sample vial 130 may be flagged as unusable. The updated failure count and/or flag may be maintained within a memory of the analyzer 105. In addition or alternatively, the failure count and/or flag may be communicated to the server 110 and stored in a record of the sample database 135 that is associated with the level A sample vial 130.

Following the second failure, the operator may be instructed to select a new level A sample vial 130. For example, the image 505 of FIG. 5B may be communicated to the operator via the input/display section 120. The operations may then repeat from block 400.

The rational for retesting after the first failure is that in some instances, a level A sample vial 130 may result in a failure because the level A sample vial 130 was not mixed properly. In this situation, the substances within the level A sample vial 130 may not be evenly distributed throughout the level A sample vial 130. Heavier substances will tend to accumulate at the bottom of the level A sample vial 130. A needle through which the sample is drawn by the measurement hardware 128 tends to draw the sample from near the bottom of the level A sample vial 130. Under these circumstances, an increased quantity of heavier substances will be withdrawn, thus causing the failure. However, as a result of the uneven distribution of the substances, the various ratios of substances will change unevenly. In other words, the relative concentrations of the substances within the level A sample vial 130 will change. This may render the level A sample vial 130 unusable for future quality control checks. In some implementations, one failure may be tolerated provided the operator subsequently mixes the level A sample vial 130 thoroughly on the second attempt. However, after a subsequent failure, the level A sample vial 130 may be rendered unusable for future quality control checks. The number of times a given level A sample vial 130 may be allowed to fail may be greater in some instances. For example, the size of the level A sample vial 130 or the manner in which a sample is withdrawn may be configured so that more than one failure is tolerable.

Returning to block 405, if the level A sample vial 130 passes the quality control check, then at block 430, a level B sample vial 132 is tested. The level B sample vial 132 is tested in the same manner as the level A sample vial 130. That is, if the level B sample vial 132 fails a first quality control check, a failure count specifically associated with the level B sample vial 132 is incremented by one and the operator is instructed to perform the quality control check a second time. If the quality control check fails a second time, the operator is instructed to select a new level B sample vial 132 for quality control checking. In certain examples, if the second vial (e.g., level B sample vial 132) fails the quality control (QC) measurement and the number of times the second vial has failed the QC measurement is not within a second predetermined number, the controller 127 is configured to communicate, via the display 120, instructions to contact service personnel.

At block 435, after a level A sample vial 130 and a level B sample vial 132 vial have passed the quality control checks, then a flag may be set to indicated that a further quality control check is not required for a certain period. In some implementations, the flag is reset on a periodic basis, such as on a twenty-four hour cycle or at a specific time of day.

At block 440, the analyzer 105 is ready for normal operations. That is, an operator may begin measuring actual patient blood samples.

Thus, the operations above minimize the wasting of level A sample vials 130 and level B sample vials 132 by allowing for a given sample vial to fail a specified number of times before the sample vial is flagged as being unusable. This in turn helps to reduce lower operating costs.

Figure 6:
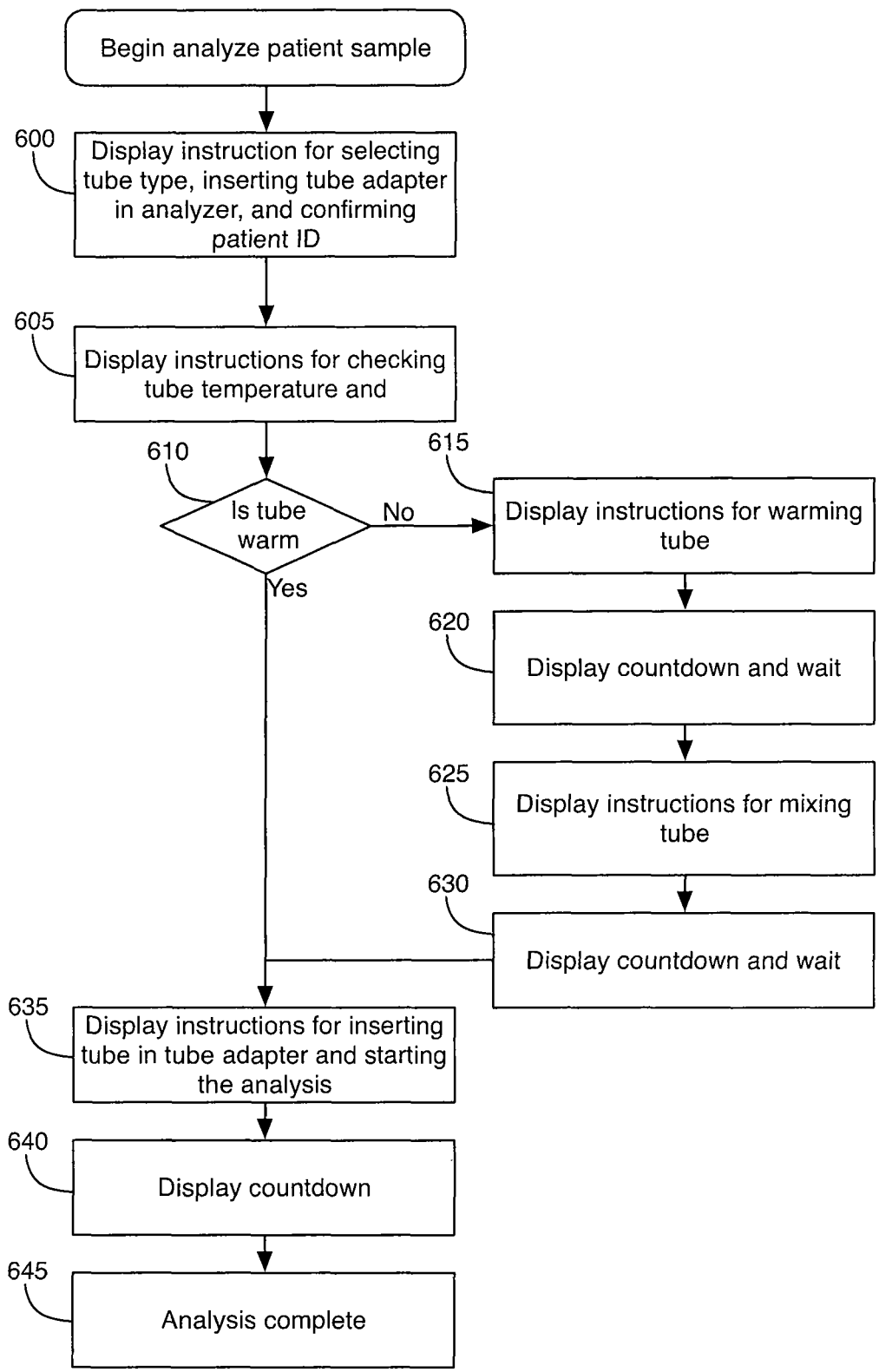
FIG. 6 is an exemplary block diagram for instructing an operator on the correct pre-analytical procedures of a sample.

FIG. 6 illustrates exemplary operations that may be performed by the analyzer 105 for the pre-analytical procedures of a patient sample. Pre-analytical procedures of a patient sample may be required in some instances to ensure accurate measurement of the patient sample. The operations in FIG. 6 are best understood with reference to FIGS. 7A-13A. Computer instructions for executing the operations may be stored in one or more non-transitory computer readable media of the analyzer 105, such as a computer memory that is in communication with the controller 127. The instructions may be executed by the controller 127 or any of the systems or processors described herein.

Figure 7A:
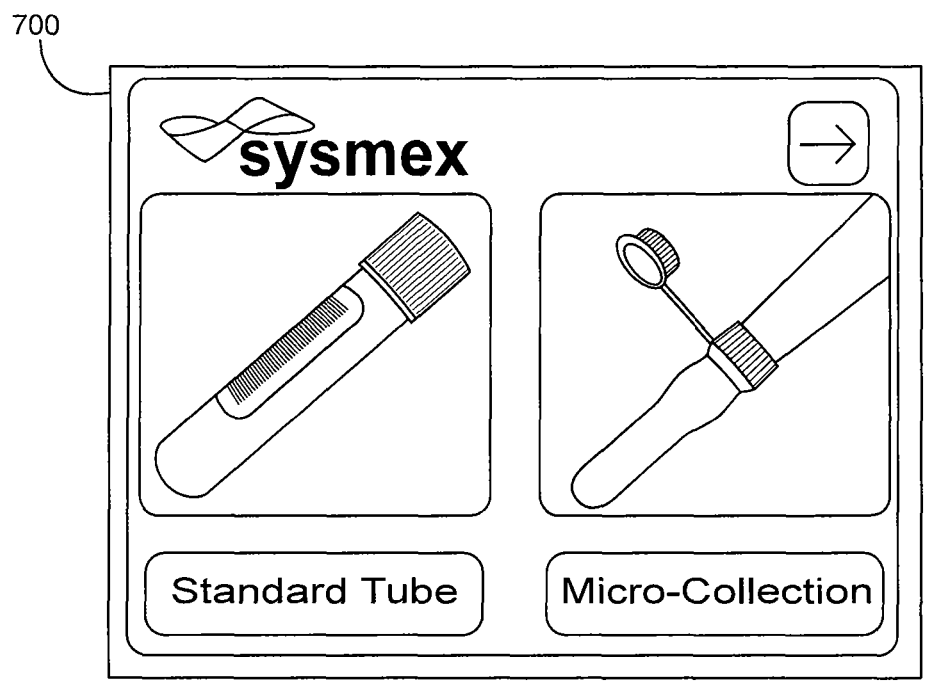
Figure 7B:
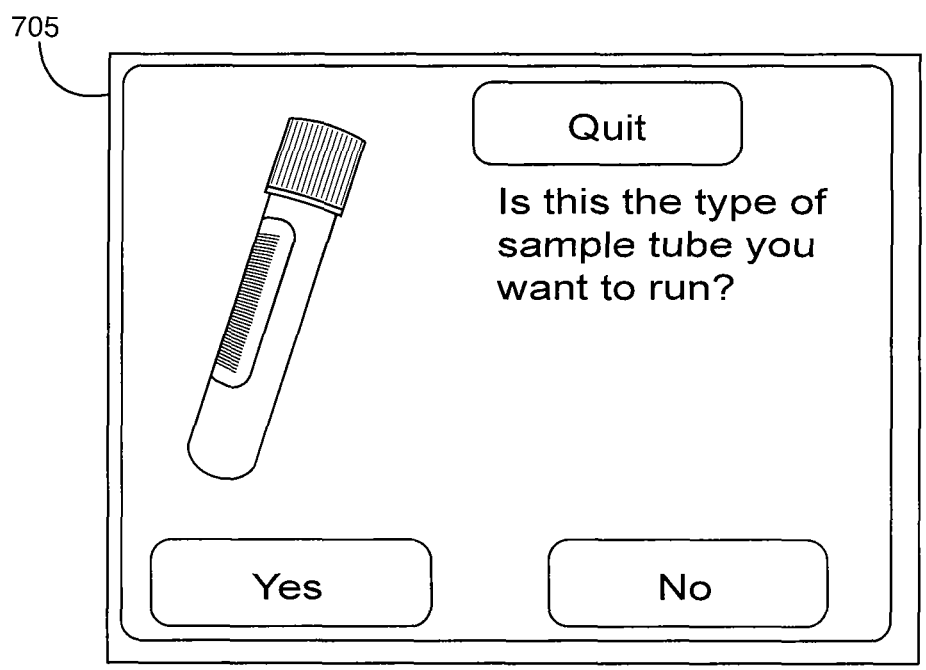

At block 600, the operator specifies a type of patient sample vessel to be tested. FIG. 7A illustrates an exemplary image 700 that may be shown to the operator via the input/display section 120. In the exemplary image 700, the operator specifies that the blood is either in a standard test tube or in a micro-collection tube. The standard tube may hold patient blood that was sampled several days prior testing, whereas the blood in the micro-collection tube may have just been obtained. In the case of a standard tube, the blood may have settled into its constituent components. For example, the blood platelets may accumulate towards the bottom of the test tube. To ensure accurate measurement of the patient blood sample, the test tube must be shaken to evenly distribute the blood constituents.

After being presented with the different patient sample vessel options, the operator selects the desired vessel. A confirmation image (See FIG. 7B) may be presented to the operator to confirm the desired vessel selection.

Figure 8A:
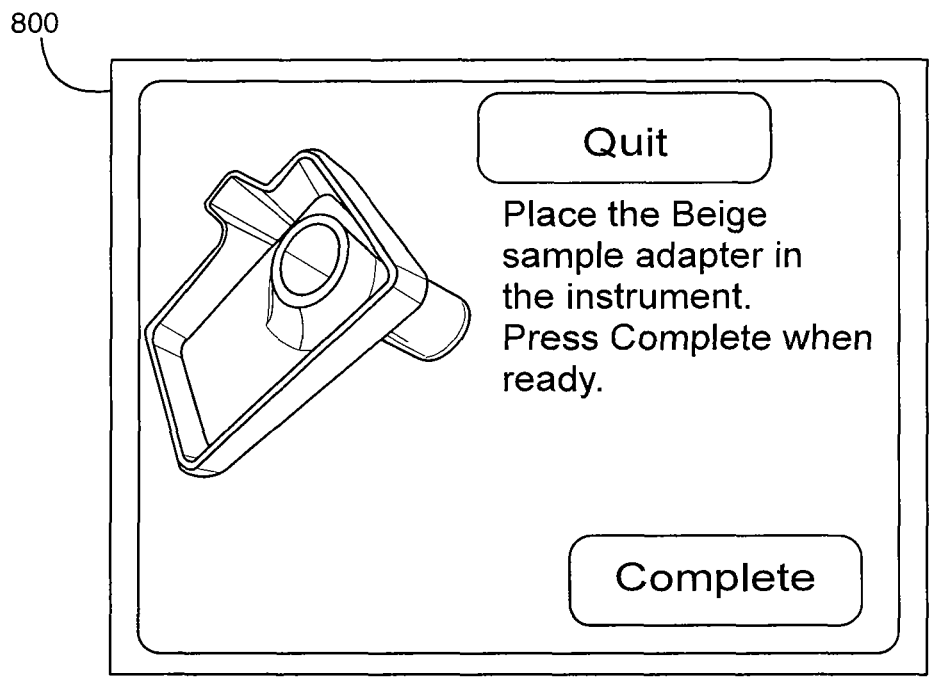

The operator may then be provided with instructions for inserting vessel adapter into the analyzer 105. For example, as illustrated in FIG. 8A, an image 800 that includes instructions along with graphical depictions for inserting the vessel adapter may be presented on the input/display section 120. Once the operator completes this procedure, the operator may indicate that this procedure is complete.

Figure 8B:
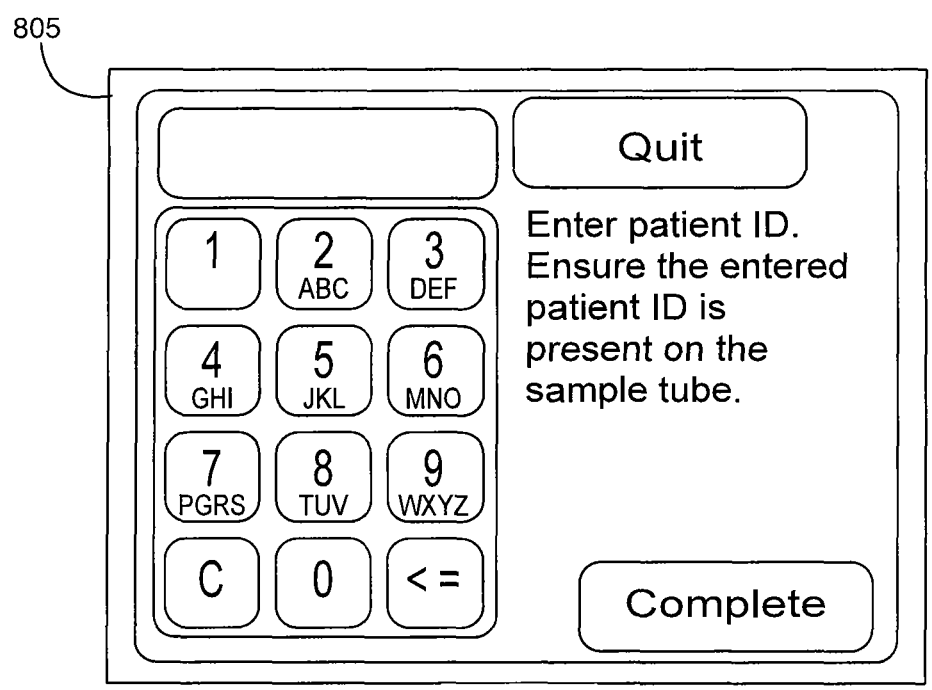

The operator may then enter an ID associated with the patient. For example, as illustrated in FIG. 8B, an image 805 that includes a numeric keypad along instructions for specifying the patient ID may be presented on the input/display section 120. Once the operator completes this procedure, the operator may indicate that this procedure is complete. In some implementations, the operator may be asked to confirm the patient ID (See FIG. 9A). For example, the analyzer 105 may determine that the ID is new and request confirmation before generation of a record of data for the new patient.

Figure 9A:
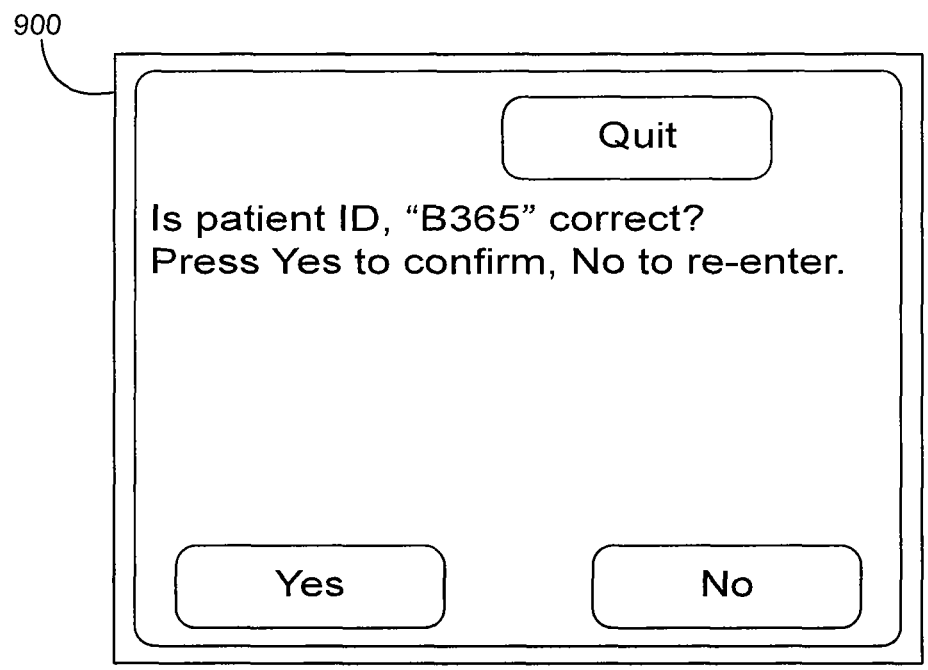
Figure 9B:
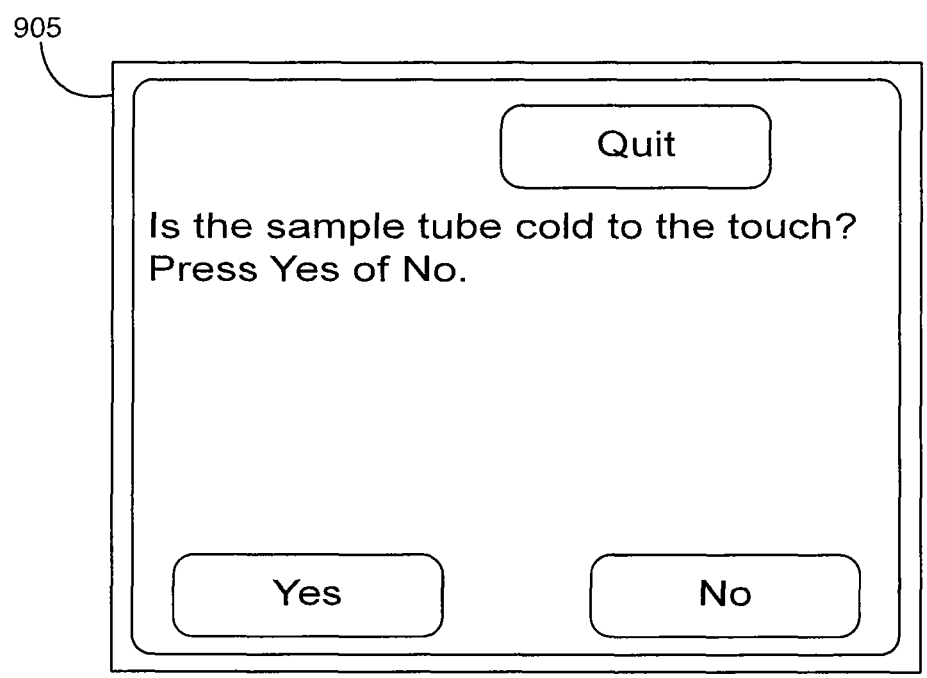

At block 605, the operator may be instructed to check the temperature of the patient blood sample. For example, as illustrated in FIG. 9B, the operator may be presented with an image 905 via the input/display section 120 that includes instructions. The instructions may ask the operator whether the patient blood sample is cold to the touch. The temperature of the patient blood sample may indicate whether the patient blood sample was recently acquired or whether the patient blood sample was in storage. As noted above, a recently acquired patient blood sample may still be mixed relatively thoroughly, which will result in more accurate testing of the blood. On the other hand, a patient blood sample that was stored may have separated into its constituent components. In this case, some additional processing may be required before testing the patient blood sample, as described below.

Figure 10A:
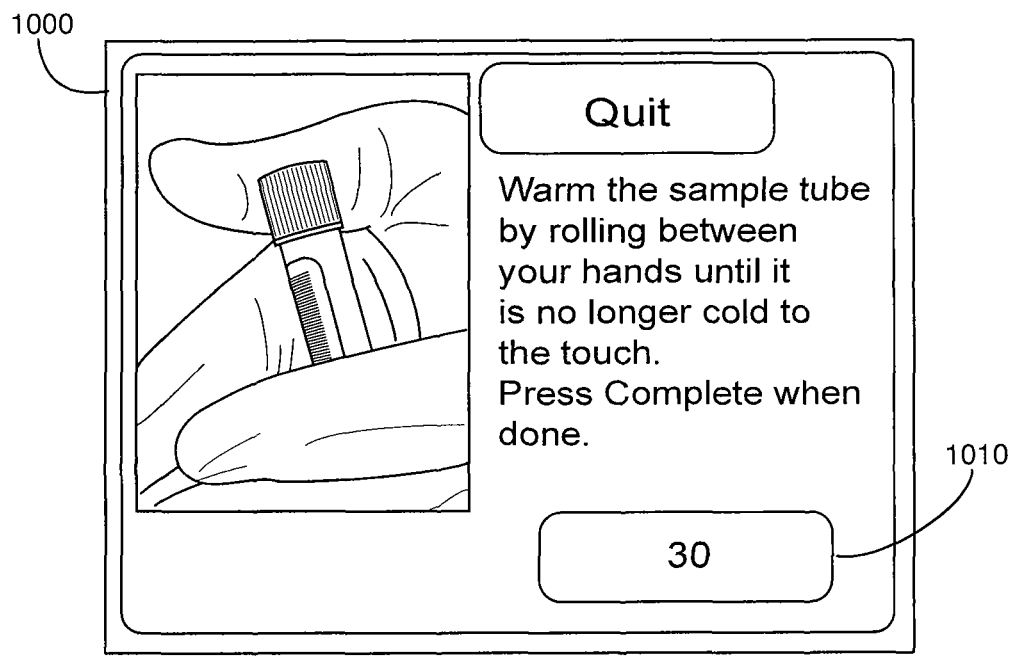

If at block 610, the patient blood sample is cold to the touch, then at block 615, the operator may be presented with instructions for warming the patient blood sample. For example, as illustrated in FIG. 10A, an image 1000 with instructions for warming the patient blood sample may be presented to the operator via the input/display section 120. The instructions may indicate that the operator is to warm the patient blood sample between his fingers until the patient blood sample is no longer cold to the touch.

At block 620, a graphical button 1010 for specifying that the warming is complete is presented to the operator. The graphical button 1010 may initially display a numeric value corresponding to a timer countdown value in seconds. The initial value may correspond to a pre-determined time necessary for performing the current procedure. For example, the pre-determined time necessary for warming the patient blood sample may be thirty seconds. The initial value may be a time longer than the pre-determined time necessary for warming the patient blood sample.

The value shown on the graphical button 1010 may slowly decrement until reaching zero. While counting down, the graphical button 1010 may be unresponsive to operator input, thus preventing the operator from quickly skipping ahead to the final steps for testing the patient blood sample. This in turn increases the likelihood that the operator will actually warm the patient blood sample as instructed.

Figure 10B:
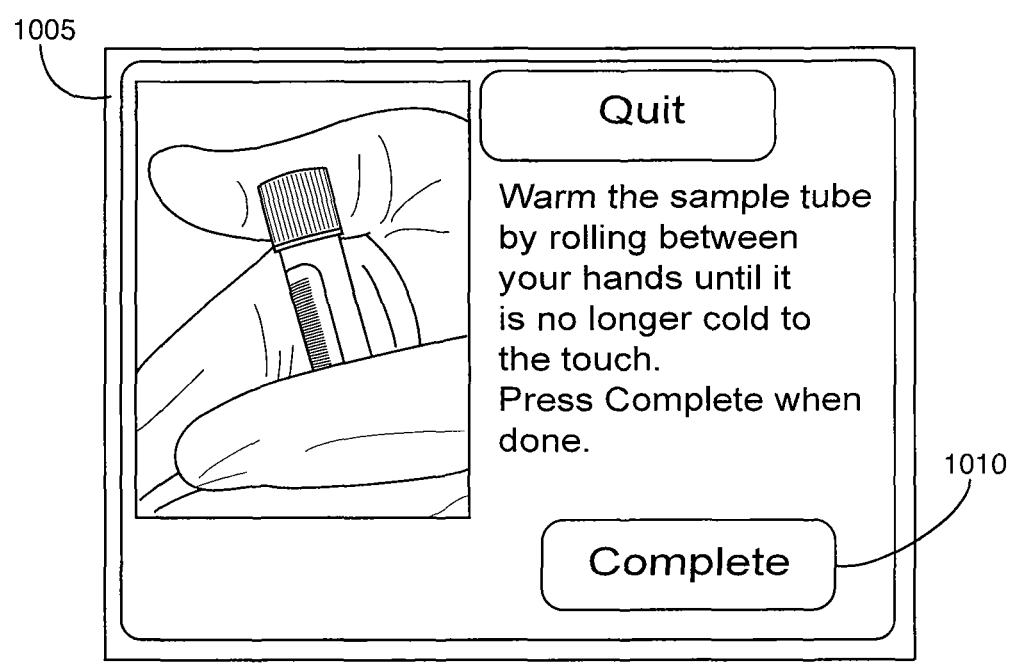

Once the countdown is completed, the text "complete" may be displayed on the graphical button 1010, as illustrated in FIG. 10B. The operator may then select the graphical button 1010 to proceed.

Figure 11A:
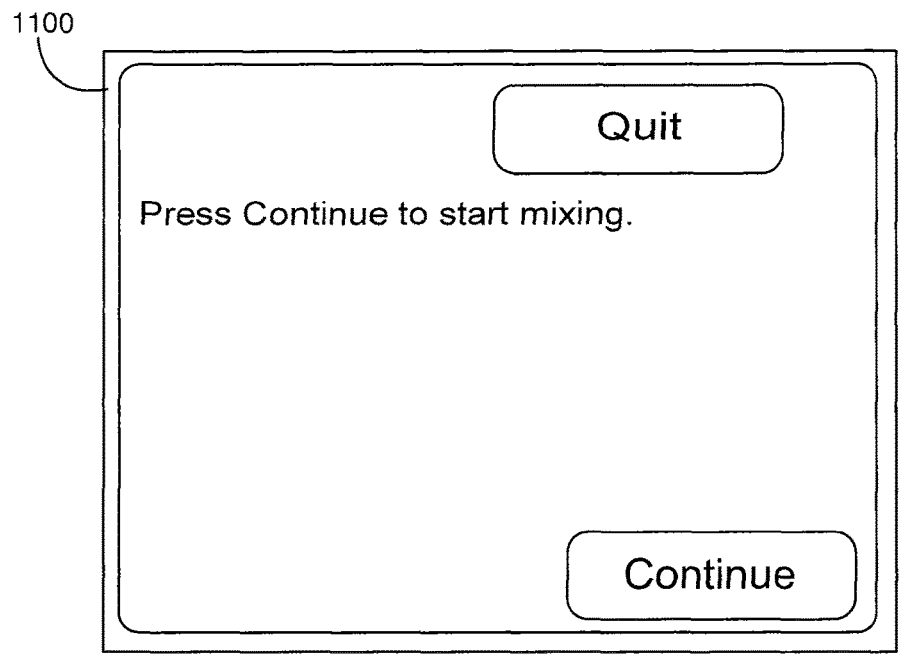

At block 625, the operator may be presented with instructions for mixing the patient blood sample. For example, as illustrated in FIG. 11A, an image 1100 with instructions for starting a mixing process may be presented to the operator via the input/display section 120. The instructions may ask the operator whether to continue on to a mixing process.

Figure 11B:
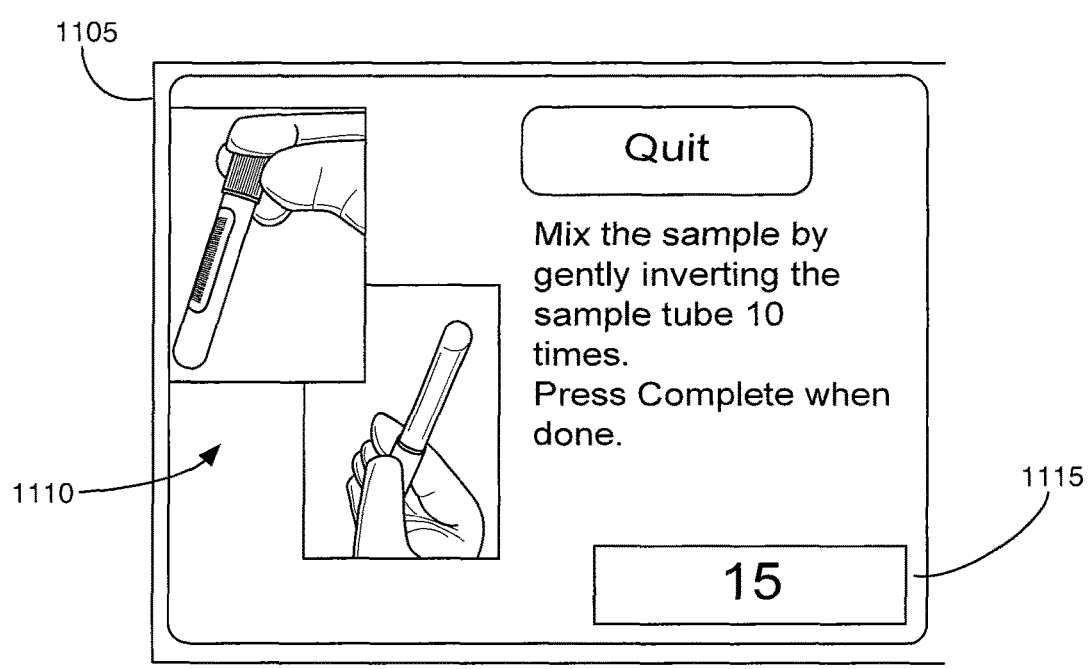

If the operator continues, the operator may be presented with instructions for mixing the patient blood sample. For example, as illustrated in FIG. 11B, an image 1105 with instructions for mixing the patient blood sample may be presented to the operator via the input/display section 120. A graphical depiction 1110 may indicate the manner in which the operator is to mix the patient blood sample.

At block 630, a graphical button 1115 for specifying that the mixing is complete is presented to the operator. The graphical button 1115 may initially display a numeric value corresponding to a timer countdown value in seconds. The initial value may correspond to a pre-determined time necessary for performing the current procedure. For example, the pre-determined time necessary for mixing the patient blood sample may be fifteen seconds.

The value presented on the graphical button 1115 may slowly decrement until reaching zero. While counting down, the graphical button 1115 may be unresponsive to operator input, thus preventing the operator from quickly skipping ahead to the final steps for testing the patient blood sample. This in turn increases the likelihood that the operator will actually mix the patient blood sample as instructed.

Figure 12A:
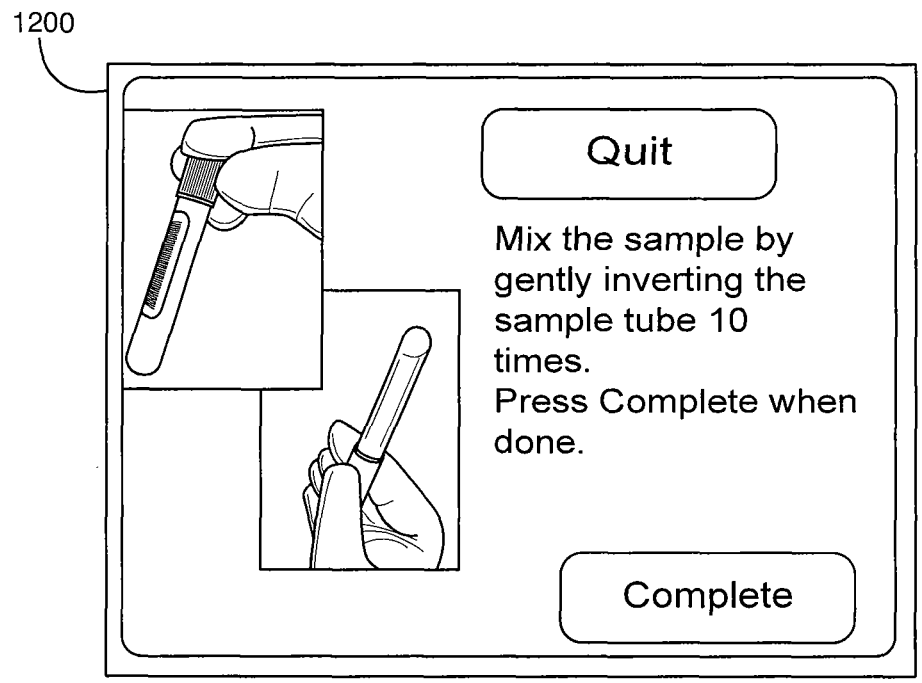
Figure 12B:
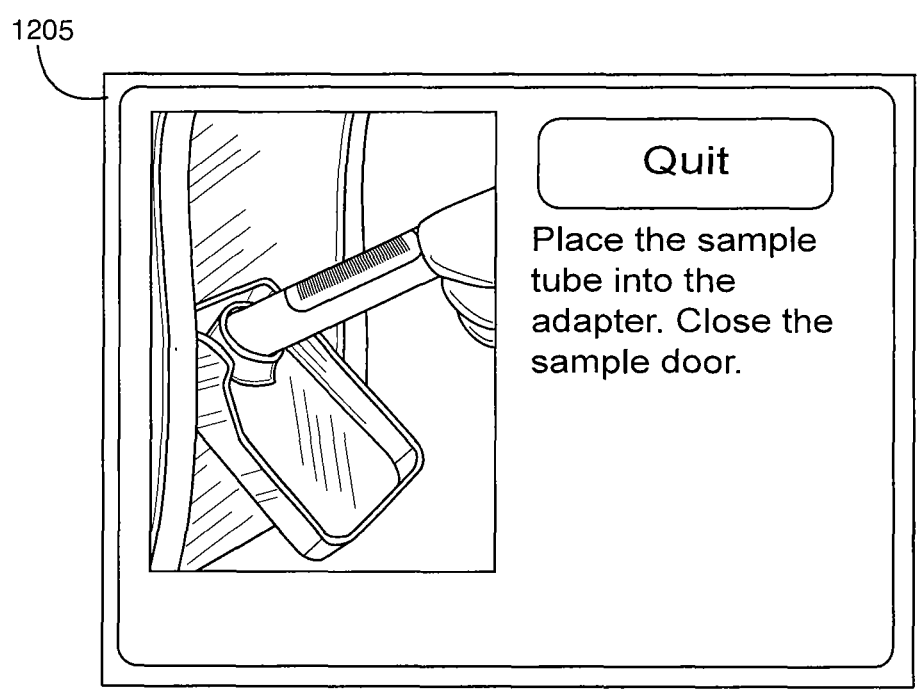
Figure 13A:
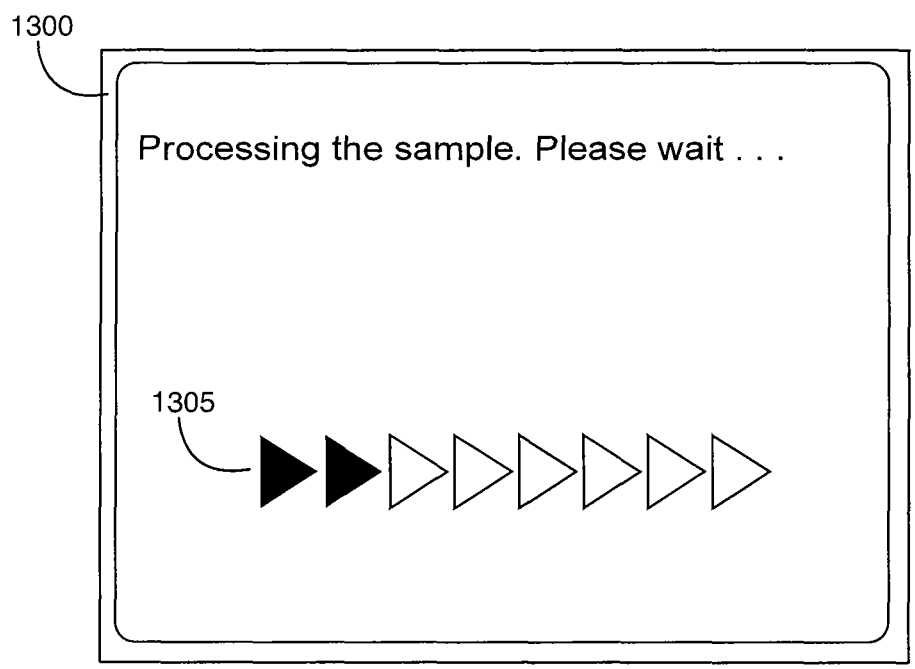

At block 635, the operator may be presented with instructions for inserting the patient blood sample in the sample-setting panel 125 of the analyzer 105. For example, as illustrated in FIG. 12B, an image 1205 with instructions for inserting the sample tube and a graphical depiction of the same may be presented to the operator via the input/display section 120.

At block 640, the operator may be presented with an image 1300 (FIG. 13A) that displays a progress bar 1305. The image may be automatically generated after the operator closes the sample-setting panel 125. The progress bar 1305 is configured to represent to the operator the relative progress of the testing.

At block 645, the progress bar 1305 may indicate that the analysis is complete. Once complete, an analysis report may be communicated to the operator. For example, a printer (not shown) attached to the analyzer 105 may print the results of the analysis. In addition or alternatively, the analysis report may be communicated to others electronically. For example, the analysis may be emailed to a doctor, hospital, and the like.

Returning to block 610, if the patient blood sample is already warm to the touch, the operations at blocks 615 through 630 may be skipped, and the operations may continue from block 635.

Thus, the operations above help ensure accurate testing of a patient blood sample by instructing an operator on pre-analytical procedures of the patient blood sample. The operations help to ensure that the operator performs certain pre-analytical procedures for a pre-determined amount of time.

Figure 14:
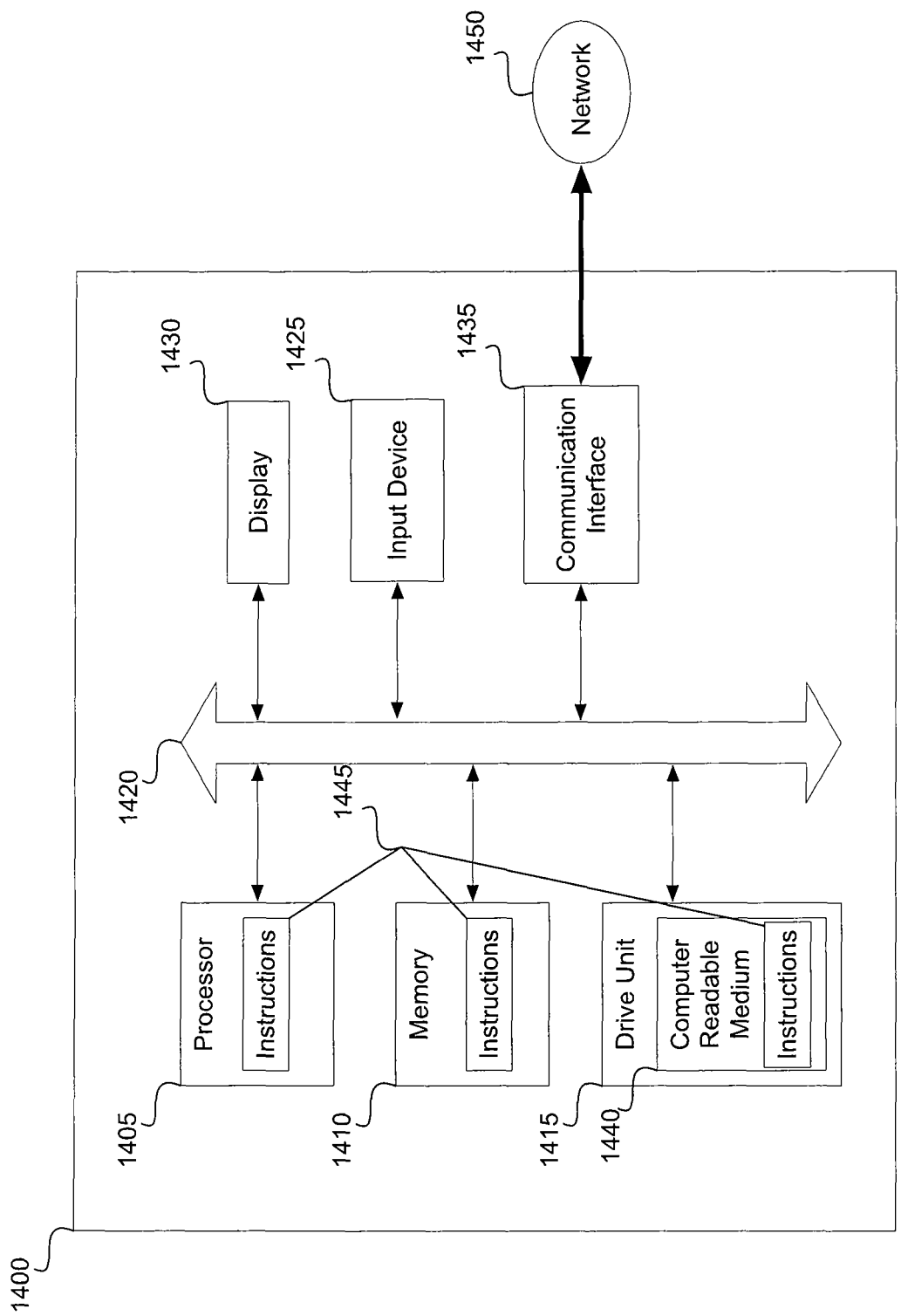
FIG. 14 illustrates a general computer system that may represent any of the computing devices referenced herein.

FIG. 14 illustrates a general computer system 1400, which may represent portions of the analyzer 105, such as the controller 127 or the sever or any other computing devices referenced herein. The computer system 1400 may include a set of instructions 1445 that may be executed to cause the computer system 1400 to perform any one or more of the methods or computer-based functions disclosed herein. The computer system 1400 may operate as a stand-alone device or may be connected, e.g., using a network, to other computer systems or peripheral devices.

In a networked deployment, the computer system 1400 may operate in the capacity of a server or as a client-operator computer in a server-client operator network environment, or as a peer computer system in a peer-to-peer (or distributed) network environment. The computer system 1400 may also be implemented as or incorporated into various devices, such as a personal computer or a mobile device, capable of executing a set of instructions 1445 (sequential or otherwise) that specify actions to be taken by that machine. Further, each of the systems described may include any collection of sub-systems that individually or jointly execute a set, or multiple sets, of instructions to perform one or more computer functions.

The computer system 1400 may include one or more memory devices 1410 on a bus for communicating information, such as the sample database 135 (FIG. 1) and/or operator database 140 (FIG. 1). In addition, code operable to cause the computer system to perform any of the acts or operations described herein may be stored in the memory 1410. The memory 1410 may be a random-access memory, read-only memory, programmable memory, hard disk drive or any other type of memory or storage device.

The computer system 1400 may include a display 1430, such as a liquid crystal display (LCD), a cathode ray tube (CRT), or any other display suitable for conveying information. The display 1430 may act as an interface for the operator to see the functioning of the processor 1405, or specifically as an interface with the software stored in the memory 1410 or in the drive unit 1415.

Additionally, the computer system 1400 may include an input device 1425, such as a keyboard or mouse, configured to allow an operator to interact with any of the components of system 1400.

The computer system 1400 may also include a disk or optical drive unit 1415, such as the high-latency storage 110 (FIG. 1). The disk drive unit 1415 may include a computer-readable medium 1440 in which one or more sets of instructions 1445, e.g. software, can be embedded. Further, the instructions 1445 may perform one or more of the operations as described herein. The instructions 1445 may reside completely, or at least partially, within the memory 1410 and/or within the processor 1405 during execution by the computer system 1400. The memory 1410 and the processor 1405 also may include computer-readable media as discussed above.

The computer system 1400 may include a communication interface 1435 that enables communications via a network 1450. The network 1450 may include wired networks, wireless networks, or combinations thereof. The communication interface 1435 network may enable communications via any number of communication standards, such as 802.11, 802.12, 802.20, WiMax, cellular telephone standards, or other communication standards.

Accordingly, the method and system may be realized in hardware, software, or a combination of hardware and software. The method and system may be realized in a centralized fashion in at least one computer system or in a distributed fashion where different elements are spread across several interconnected computer systems. Any kind of computer system or other apparatus adapted for carrying out the methods described herein is suited. A typical combination of hardware and software may be a general-purpose computer system with a computer program that, when being loaded and executed, controls the computer system such that it carries out the methods described herein.

The method and system may also be embedded in a computer program product, which includes all the features enabling the implementation of the operations described herein and which, when loaded in a computer system, is able to carry out these operations. Computer program in the present context means any expression, in any language, code or notation, of a set of instructions intended to cause a system having an information processing capability to perform a particular function, either directly or after either or both of the following: a) conversion to another language, code or notation; b) reproduction in a different material form.

While the method and system has been described with reference to certain embodiments, it will be understood by those skilled in the art that various changes may be made and equivalents may be substituted without departing from the scope. In addition, many modifications may be made to adapt a particular situation or material to the teachings without departing from its scope. Therefore, it is intended that the present method and system not be limited to the particular embodiment disclosed, but that the method and system include all embodiments falling within the scope of the appended claims.

We claim:

1. A hematology analyzer for measuring a blood sample, the hematology analyzer comprising:
   a display;
   measurement hardware configured to measure blood constituents contained in a blood sample collected from a subject; and
   a controller in communication with the display and the measurement hardware, the controller configured to:
   control the display to indicate an instruction to implement a first quality control (QC) measurement on a first vial containing a first QC sample;
   control the display to indicate an instruction to repeat the first QC measurement on the first vial if a result of the first QC measurement on the first QC sample by the measurement hardware is not within a first predetermined range and a number of times that the result of the first QC measurement is not within the first predetermined range is less than a predetermined number greater than one;
   control the display to indicate an instruction to implement a second QC measurement on a second vial that contains a second QC sample having a consistency that substantially matches the first QC sample of the first vial if the result of the first QC measurement on the first QC sample, by the measurement hardware, that has been measured is not within the first predetermined range and the number of times is greater than or equal to the predetermined number;
   control the display to indicate an instruction to implement a third QC measurement on a third vial that contains a third QC sample having a different concentration from the first QC sample if a result of the second QC measurement on the second QC sample, by the measurement hardware, that has been measured is within the first predetermined range; and
   control the measurement hardware to allow measurements of the blood sample collected from the subject to be performed if a result of the third QC measurement on the third QC sample, by the measurement hardware, that has been measured is within a second predetermined range.

2. The hematology analyzer according to claim 1, wherein if the result of the second QC measurement that has been measured is not within the first predetermined range and a second number of times that the result of the second QC measurement is not within the first predetermined range is less than a second predetermined number greater than one, the controller is configured to communicate instructions for repeating the second QC measurement on the second vial via the display, and if the result of the second QC measurement on the second vial, by the measurement hardware, that has been measured is not within the first predetermined range and the second number of times is greater than or equal to the second predetermined number, the controller is configured to communicate, via the display, instructions to contact service personnel.

3. The hematology analyzer according to claim 1, wherein the predetermined number is two and the controller is configured not to communicate the instructions to perform the second QC measurement on the second vial before the number of times is greater than or equal to the predetermined number.

4. The hematology analyzer according to claim 1, wherein the controller is configured to store the number of times that the result of the first QC measurement is not within the first predetermined range.

5. The hematology analyzer according to claim 4, wherein the controller is configured to store a flag that the first vial is unusable if the number of times that the result of the first QC measurement is greater than or equal to the predetermined number.

6. The hematology analyzer according to claim 1, wherein the controller is configured to communicate information that defines whether the first vial fails the first QC measurement to a server that comprises a sample database that stores data that specifies information related to the first vial.

7. The hematology analyzer according to claim 6, wherein the controller is configured to communicate the number of times that the result of the first QC measurement is not within the first predetermined range to the server.

8. The hematology analyzer according to claim 7, wherein the controller is configured to communicate instructions to the server to mark the first vial as unusable if the number of times that the result of the first QC measurement is greater than or equal to the predetermined number.

9. The analyzer hematology according to claim 6, further comprising a barcode reader, wherein the controller is configured to communicate with the server to specify known quantities of substances in the first QC sample in the first vial in response to reading a barcode on the first vial by the barcode reader.

10. The analyzer hematology according to claim 1, wherein the controller is configured to control the display to indicate an instruction to implement the third QC measurement on the third vial if the result of the first QC measurement on the first QC vial, by the measurement hardware, that has been measured is within the first predetermined range.

11. A method for measuring a blood sample, comprising:
measuring, by measurement hardware of a hematology analyzer, blood constituents contained in a blood sample collected from a subject; and
displaying, on the hematology analyzer, an instruction to implement a first quality control (QC) measurement on a first vial containing a first QC sample;
displaying, on the hematology analyzer, an instruction to repeat the first QC measurement on the first vial in response to a result of the first QC measurement on the first QC sample by the measurement hardware is not within being outside of a first predetermined range and a number of times that the result of the first QC measurement is not within the first predetermined range being less than a predetermined number greater than one; and
displaying, on the hematology analyzer, an instruction to implement a second QC measurement on a second vial that contains a second QC sample having a consistency that substantially matches the first QC sample of the first vial in response to the result of the first QC measurement on the first QC sample, by the measurement hardware, that has been measured being outside the first predetermined range and the number of times being greater than or equal to the predetermined number;
displaying, on the hematology analyzer, an instruction to implement a third QC measurement on a third vial that contains a third QC sample having a different concentration from the first QC sample in response to the result of the second QC measurement on the second QC sample, by the measurement hardware, that has been measured being within the first predetermined range; and
controlling the measurement hardware to allow measurements of the blood sample collected from the subject to be performed in response to a result of the third QC measurement on the third QC sample, by the measurement hardware, that has been measured being within a second predetermined range.

12. The method according to claim 11, wherein the predetermined number is two.

13. A system comprising:
a hematology analyzer for measuring a blood sample; and
a server in communication with the hematology analyzer via a network,
the hematology analyzer comprising:
a display;
a barcode reader;
measurement hardware configured to measure blood constituents contained in a blood sample collected from a subject; and
a controller in communication with the display and the measurement hardware, the controller configured to:
control the display to indicate an instruction to implement a first quality control (QC) measurement in which the measurement hardware measures a quantity of a substance in a first QC sample contained in a first vial having a first barcode;
communicate with the server to send data of the first barcode read by the barcode reader and to receive a first known quantity of the substance in the first QC sample;
control the display to indicate an instruction to repeat the first QC measurement on the first vial if a result of a first QC measurement on the first QC sample by the measurement hardware is not within a first acceptable range of the first known quantity and a number of times that the result of the first QC measurement is not within the first acceptable range is less than a predetermined number greater than one;
control the display to indicate an instruction to implement a second QC measurement in which the measurement hardware measures a quantity of a substance in a second QC sample which is contained in a second vial having a second barcode and has a consistency that substantially matches the first QC sample of the first vial if a result of the first QC measurement on the first QC sample, by the measurement hardware, that has been measured is not within the first acceptable range and the number of times is greater than or equal to the predetermined number;
communicate with the server to send data of the second barcode read by the barcode reader and to receive the first known quantity of the substance in the second QC sample;
control the display to indicate an instruction to implement a third QC measurement in which the measurement hardware measures a quantity of a substance in a third QC sample which is contained in a third vial having a third barcode and contains a different quantity of the substance in the first QC sample if a result of the second QC measurement on the second QC sample, by the measurement hardware, that has been measured is within the first acceptable range of the first known quantity;
communicate with the server to send data of the third barcode scanned by the barcode reader and to receive a second known quantity of the substance in the third QC sample; and
control the measurement hardware to allow measurements of the blood sample collected from the subject to be performed if a result of the third QC measurement on the third QC sample, by the measurement hardware, that has been measured is within a second acceptable range of the second known quantity.

14. The system according to claim 13, wherein the controller is configured to control the display to indicate an instruction to implement the third QC measurement on the third vial if any of the results of the first QC measurement on the first QC vial, by the measurement hardware, that has been measured is within the first predetermined range.

* * * * *